US012636256B2

(12) United States Patent

Li et al.

(10) Patent No.: US 12,636,256 B2

(45) Date of Patent: May 26, 2026

(54) STARCH FILM-FORMING COMPOSITIONS AND METHODS OF THEIR USE FOR PREPARING CAPSULE SHELLS

(71) Applicant: SIRIO PHARMA CO., LTD., Shantou (CN)

(72) Inventors: Xufa Li, Shantou (CN); Qiong Chen, Shantou (CN); Xuteng Yang, Shantou (CN); Jiewei Chen, Shantou (CN)

(73) Assignee: SIRIO PHARMA CO., LTD., Shantou (CN)

( * ) Notice: Subject to any disclaimer, the term of this patent is extended or adjusted under 35 U.S.C. 154(b) by 879 days.

(21) Appl. No.: 17/792,843

(22) PCT Filed: Dec. 28, 2021

(86) PCT No.: PCT/CN2021/142077

§ 371 (c)(1),
(2) Date: Jul. 14, 2022

(87) PCT Pub. No.: WO2022/143667

PCT Pub. Date: Jul. 7, 2022

(65) Prior Publication Data

US 2023/0051942 A1    Feb. 16, 2023

(30) Foreign Application Priority Data

Dec. 31, 2020    (CN) .......................... 202011619863.9

(51) Int. Cl.

| | |
|---|---|
| *A61K 9/48* | (2006.01) |
| *A23L 29/231* | (2016.01) |
| *A23L 29/238* | (2016.01) |
| *A23L 29/244* | (2016.01) |
| *A23L 29/256* | (2016.01) |
| *A23P 10/30* | (2016.01) |
| *A61K 47/36* | (2006.01) |

(52) U.S. Cl.

CPC .......... *A61K 9/4816* (2013.01); *A23L 29/231* (2016.08); *A23L 29/238* (2016.08); *A23L 29/244* (2016.08); *A23L 29/256* (2016.08); *A23P 10/30* (2016.08); *A61K 47/36* (2013.01)

(58) Field of Classification Search

None

See application file for complete search history.

(56) References Cited

U.S. PATENT DOCUMENTS

| | | | |
|---|---|---|---|
| 8,231,921 | B2 | 7/2012 | Bezanson et al. |
| 8,765,167 | B2 | 7/2014 | Myers et al. |
| 9,107,432 | B2 | 8/2015 | Müller et al. |
| 2005/0196436 | A1 | 9/2005 | Chantranukul |
| 2010/0240724 | A1 | 9/2010 | Chang |
| 2016/0136101 | A1 | 5/2016 | Sydow |
| 2016/0151243 | A1 | 6/2016 | Sydow |

| | | | |
|---|---|---|---|
| 2017/0172931 | A1 | 6/2017 | Kim |
| 2017/0224707 | A1 | 8/2017 | Kuusisto et al. |
| 2019/0117781 | A1 | 4/2019 | Tian |
| 2021/0128481 | A1 | 5/2021 | Zhang |
| 2021/0196641 | A1 | 7/2021 | Obatake |

FOREIGN PATENT DOCUMENTS

| | | | |
|---|---|---|---|
| CN | 1663989 | A | 9/2005 |
| CN | 1995115 | * | 7/2007 |
| CN | 101406704 | A | 4/2009 |
| CN | 100528950 | C | 8/2009 |
| CN | 102365159 | A | 2/2012 |
| CN | 104721167 | A | 6/2015 |
| CN | 104873977 | A | 9/2015 |
| CN | 105263462 | A | 1/2016 |
| CN | 106456558 | A | 2/2017 |
| CN | 108659137 | A | 10/2018 |
| CN | 110494455 | A | 11/2019 |
| CN | 112494453 | A | 3/2021 |
| CN | 113121889 | A | 7/2021 |
| CN | 113332257 | A | 9/2021 |
| CN | 113398088 | A | 9/2021 |
| CN | 113768137 | A | 12/2021 |
| EP | 1792939 | A1 | 11/2006 |
| EP | 1570843 | B1 | 9/2011 |
| EP | 2815744 | A1 | 12/2014 |
| EP | 2815745 | A1 | 12/2014 |
| EP | 3010493 | B1 | 8/2019 |

(Continued)

OTHER PUBLICATIONS

English translation of CN 101406704 (2024).*
English translation of CN1995115A (2025).*
Bowen P: "Particle Size Distribution Measurement from Millimeters to Nanometers and from Rods to Platelets", Journal of Dispersion Science and Technology, Taylor and Francis Group, New York, NY, US, vol. 23, No. 5, Jan. 1, 2002 (Jan. 1, 2002), pp. 631-662.
Chen Fengfeng et al. Rice starch granule/chitosan composite preparation of microcapsules Applied Chemical Industry vol. 45 Oct. 2016.
Qiang Minghui et al. Development of glue viscosity control system based on capsule shell production line Automation and Instrumentation Issue 8, 2015.

*Primary Examiner* — Anna R Falkowitz

*Assistant Examiner* — Garen Gotfredson

(74) *Attorney, Agent, or Firm* — Lowenstein Sandler LLP

(57) ABSTRACT

The present invention provides starch film-forming compositions and methods of their use for preparing capsule shells. The starch film-forming composition includes a gellan gum and at least one starch, wherein the total acyl content of the gellan gum ranges from 14 to 34%. The starch film-forming composition of the present invention has the advantages of desired film-forming strength and toughness, which can be applied in soft capsules to obtain soft capsules with a desired adhesive property upon formation and encapsulation property and which is free of animal-derived ingredients. The soft capsules thus are suitable for all ethnic populations in the world and can be applied globally.

19 Claims, No Drawings

(56)     References Cited

FOREIGN PATENT DOCUMENTS

| | | | |
|---|---|---|---|
| EP | 3735707 | A1 | 11/2020 |
| EP | 4134072 | A1 | 12/2021 |
| JP | 2005281687 | A | 10/2005 |
| JP | 200715851 | A | 6/2007 |
| JP | 2007153851 | A | 6/2007 |
| JP | 2007153889 | A | 6/2007 |
| JP | 2009040716 | A | 2/2009 |
| JP | 2013537902 | A | 10/2013 |
| JP | 2016199737 | A | 12/2016 |
| JP | 2018008886 | A | 1/2018 |
| TW | 201944985 | A | 12/2019 |
| WO | 9964468 | A1 | 12/1999 |
| WO | 00/31146 | A1 | 6/2000 |
| WO | 2009123257 | A1 | 10/2009 |
| WO | 2014202754 | A1 | 12/2014 |
| WO | 2014202757 | A1 | 12/2014 |
| WO | 2018177343 | A1 | 10/2018 |
| WO | 2019135606 | A1 | 7/2019 |
| WO | 2019208668 | A1 | 10/2019 |

* cited by examiner

STARCH FILM-FORMING COMPOSITIONS AND METHODS OF THEIR USE FOR PREPARING CAPSULE SHELLS

TECHNICAL FIELD

The present invention relates to the field of edible compositions, specifically to starch film-forming compositions, methods of their use for preparing capsule shells, and the prepared capsule shells.

BACKGROUND OF THE INVENTION

Soft capsules are widely used in the fields of medicines, food products, cosmetics, etc. Gelatin is widely and traditionally used as a material for soft capsules since it has excellent film-forming properties and a high mechanical strength. However, gelatin shows many drawbacks in terms of qualities during use due to its own properties. For example, gelatin molecules may be self-oxidized or cross-linked with other functional groups such as aldehyde to form a tough and flexible water-insoluble membrane on the surface of gelatin-based soft capsule, which resists the release of drugs, resulting in unqualified soft capsules in terms of disintegration. In addition, as required by a population with a religion or vegetarians, and with the outbreak of the mad cow disease and the foot-and-mouth disease around the world, efforts are always taken to develop substitutes for gelatin and a method of their use for preparing soft capsules.

For example, the Chinese Patent No. CN100528950C proposes a blend of different acyl gellan gums and a starch, comprising: a. a high acyl gellan gum; b. a low acyl gellan gum; c. a starch; and d. a plasticizer. The film prepared using such blends has a high modulus and excellent strength and elongation. The soft capsules prepared have good sealability. The high acyl gellan gum and the low acyl gellan gum as compound gelling agent can improve the strength and toughness of capsule films to some extent, but the prepared soft capsules have a low transparency, and have a seam that is not tightly sealed, making the soft capsules easy to leak oil. The Japanese Patent No. JP2007153851A proposes a composition for a soft capsule ribbon without an animal-derived component, which is obtained by mixing water, a starch and a natural gellan gum. The European Patent No. EP2815745A1 proposes a soft capsule comprising a high acyl gellan gum, at least one starch and at least one plasticizer and its preparation method. The gels formed by high acyl gellan gum have a soft texture and a high flexibility property, which in combination with a starch form a capsule shell with poor toughness, and easy to leak oil due to a thin thickness at the seam and low rupture force when shaping capsule by encapsulation. Chinese Patent No. CN 108659137 A proposes a novel gellan gum product with double setting temperatures, which has low double gel temperatures, and the formed gel has excellent gel properties and texture, which can be more widely used in the field of food products.

In conclusion, during the preparation of soft capsules with gellan gum as the major capsule materials reported in the prior art, there are many drawbacks, such as a high viscosity of the gel mass, gelling easily when stored at a high temperature, capsule shell formed with a low strength, a poor toughness, and a thin thickness at the seam and leaking oil easily after shaping capsule by encapsulation, which causes the industrial production of soft capsules unachievable.

SUMMARY OF THE INVENTION

The purpose of the present invention is to provide a starch film-forming composition comprising a gellan gum with a particular acyl content and a starch. During the research process of starch film-forming compositions, the inventors found that a gellan gum with a particular acyl content between those of high acyl gellan gum (natural gellan gum) and low acyl gellan gum has single setting temperature ranging from 20 to 75° C., so that the gel formed by the starch film-forming composition comprising the gellan gum with the particular acyl content has excellent gel properties and texture. Such gel is obviously superior to those in the prior art in terms of ribbon strength, toughness and the seam adhesive property after capsule formation in preparation of soft capsules, can fully meet the requirements for industrial production of soft capsules and can be used as an alternative in soft capsule technology. The inventors also found that starch compositions comprising a particular range of gellan gum to starch ratios are superior to starch compositions not within this range in terms of the comprehensive effect of ribbon strength, toughness and the seam adhesive property after capsule formation.

In one aspect, the present invention provides a starch film-forming composition comprising:

A. a first gelling agent;

B. a starch;

wherein the first gelling agent is a single setting temperature gellan gum with the total acyl content ranging from 14% to 34%, and the weight ratio of the single setting temperature gellan gum to the starch ranges from 0.02 to 0.5.

In one embodiment, the glyceroyl content in the total acyl groups of gellan gum ranges from 12 to 26%, and/or the acetyl content ranges from 2 to 8%.

In one embodiment, the content of starch ranges from 15 wt % to 50 wt %.

In one embodiment, the content of gellan gum ranges from 1 wt % to 8 wt %, preferably, the content of gellan gum ranges from 2 wt % to 7 wt %.

In one embodiment, the starch may be natural starch, including at least one selected from among wheat starch, waxy corn starch, pea starch, corn starch, potato starch and/or tapioca starch.

In one embodiment, the starch may be starch derivative, including at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin.

In one embodiment, the starch film-forming composition also comprises a plasticizer with a content ranging from 10 wt % to 35 wt %, preferably, including at least one selected from among glycerol, sorbitol, maltitol, erythritol, xylitol, fructose and trehalose.

In one embodiment, the starch film-forming composition also comprises a second gelling agent, preferably, including at least one selected from among carrageenan, agar, sodium alginate, pectin, high acyl gellan gum, low acyl gellan gum, konjac glucomannan, xanthan gum, locust bean gum, guar gum and pullulan; preferably the content of the second gelling agent ranges from 0.2 wt % to 3.5 wt %; preferably the pectin is at least one selected from among low methoxyl pectin, high methoxyl pectin and amide pectin; preferably, the low methoxyl pectin has a degree of esterification of DE<50%, and the amide pectin has a degree of amidation of DA 5%-25%.

In one embodiment, the starch film-forming composition comprises 35 wt % to 60 wt % water.

In another aspect, the present invention provides a method for preparing a capsule shell using the starch film-forming composition of the present invention, comprising 1) A) firstly premixing and dispersing the first gelling agent and plasticizer homogeneously, adding into water under stirring, and then heating at a temperature between 60 and 98° C. with stirring until the first gelling agent dissolves; B) adding the starch, and continuing to heat at a temperature between 60 and 98° C. with stirring until the starch dissolves; C) removing air bubbles to obtain a gel mass; 2) encapsulating; and 3) drying. Encapsulation can be carried out as follows: a soft capsule production line is employed, the gel mass is transported to a spreader box of a soft capsule encapsulation machine, the gel mass is cooled on the surface of a rotating drum to form a ribbon, then soft capsules are formed by extrusion and encapsulation when injecting the filling, and can be further shaped by a rotating cage device. Drying can be carried out as follows: capsules after forming or shaping with rotating cage are dried until the moisture content of the capsule shell is 8-25%.

In one embodiment, the step A) further comprises adding a second gelling agent; and the step A) is a step for premixing and dispersing the first gelling agent, the second gelling agent and the plasticizer homogeneously, adding into water under stirring, and then heating at a temperature between 60 and 98° C. with stirring until the first gelling agent and the second gelling agent dissolve.

In another aspect, the present invention provides a capsule shell comprising the starch film-forming compositions of the present invention.

In one embodiment, the water content of the capsule shell ranges from 8 to 25%.

In another aspect, the present invention provides use of the starch film-forming composition of the present invention in medicines, food products or cosmetics.

The present invention further comprises the following embodiments:

Embodiment 1. A starch film-forming composition comprising:

1 wt %-8 wt % of a first gelling agent;
0.2 wt %-3.5 wt % of a second gelling agent;
15 wt %-50 wt % of a starch;
10 wt %-35 wt % of a plasticizer; and
water, up to 100 wt %;

wherein the first gelling agent is at least one selected from among carrageenan, agar, sodium alginate, gellan gum, konjac glucomannan, xanthan gum, locust bean gum, guar gum and pullulan;

the second gelling agent is pectin.

Embodiment 2. The starch film-forming composition of embodiment 1, wherein the pectin is at least one selected from among low methoxy pectin, high methoxy pectin, and amide pectin.

Embodiment 3. The starch film-forming composition of the preceding embodiments, wherein the low methoxy pectin has a degree of esterification of DE <50%, or the amido pectin has a degree of amidation DA of 5-25%.

Embodiment 4. The starch film-forming composition of the preceding embodiments, wherein the gellan gum is a high acyl gellan gum, a low acyl gellan gum, or a gellan gum with a total acyl content of 14-34%, preferably the gellan gum is a gellan gum with a total acyl content of 14-34%, preferably the glyceroyl content in the total acyl groups of gellan gum is 12-26% and/or the acetyl content is 2-8%.

Embodiment 5. The starch film-forming composition of the preceding embodiments, wherein the starch is a natural starch, including at least one selected from among wheat starch, waxy corn starch, pea starch, corn starch, potato starch and tapioca starch.

Embodiment 6. The starch film-forming composition of the preceding embodiments, wherein the starch is a starch derivative, including at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin.

Embodiment 7. The starch film-forming composition of the preceding embodiments, wherein the plasticizer is at least one selected from among glycerol, sorbitol, maltitol, erythritol, xylitol, fructose and trehalose.

Embodiment 8. A method of preparing a capsule shell using the starch film-forming composition of any of embodiments 1 to 7, comprising 1) A) premixing and dispersing the first gelling agent, the second gelling agent and the plasticizer homogeneously, adding into water under stirring, and then heating at a temperature between 60 and 98° C. with stirring until the first gelling agent and the second gelling agent dissolve; B) adding the starch, and continuing to heat at a temperature between 60 and 98° C. with stirring until the starch dissolves; C) removing air bubbles to obtain a gel mass;

2) encapsulating; and
3) drying.

Embodiment 9. A capsule shell comprising the starch film-forming composition of any one of embodiments 1 to 8.

Embodiment 10. The capsule shell of embodiment 9, wherein the water content of the capsule shell ranges from 8 to 25%.

Embodiment 11. Application of the starch film-forming composition of any one of embodiments 1 to 9 in medicines, food products or cosmetics.

The advantages of the starch film-forming composition of the present invention include: good film-forming strength and toughness, which can be used in soft capsules to obtain soft capsules with good adhesive and encapsulation properties upon formation, the soft capsule which is free of animal-derived ingredients and thus is suitable for all ethnic groups in the world and can be applied globally.

DETAILED DESCRIPTION OF THE INVENTION

The following content is provided to further illustrate the present invention.

As used herein, "%" or "wt %" refers to weight percentage, unless stated to the contrary.

The present invention provides a starch film-forming composition comprising a first gelling agent and a starch, and the first gelling agent is gellan gum. Gellan gum can be classified into low acyl gellan gum, high acyl gellan gum and partially deacylated gellan gum according to the total acyl content. In the present invention, the total acyl content of gellan gum may be 14-34%, e.g. 14%, 16%, 17%, 19%, 27%, 28%, 30%, 31%, 32% or 34%. The total acyl content of gellan gum can be calculated as the sum of the content of glyceroyl and acetyl. The glyceroyl content may be 12-26%, e.g. 13%, 14%, 15%, 16%, 17%, 18%, 19%, 20%, 21%, 22%, 23%, 24% or 25%. The acetyl content may be 2-8%, e.g. 3%, 4%, 5%, 6% or 7%.

The gellan gum content in the starch film-forming composition may be 1 wt % to 8 wt %, e.g. 2 wt %, 3 wt %, 4 wt %, 5 wt %, 6 wt %, 7 wt % or 8 wt %. Preferably, the gellan gum content may be 2 wt %-7 wt %.

The starch content in the starch film-forming composition may be 15 wt % to 50 wt %, e.g. 20 wt %, 25 wt % or 35 wt %, 45 wt %.

Starch can be natural starch or starch derivative made from natural starch by physical, chemical, enzymatic methods, or combination thereof. The natural starch includes at least one selected from among wheat starch, waxy corn starch, pea starch, corn starch, potato starch and tapioca starch. The starch derivative includes at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin. For example, the contents of above various types of starch are each independently 7 wt %-50 wt %, e.g. 8 wt %, 9 wt %, 10 wt %, 11 wt %, 12 wt %, 13 wt %, 14 wt %, 15 wt %, 16 wt %, 17 wt %, 18 wt % %, 19 wt %, 20 wt %, 21 wt %, 22 wt %, 23 wt %, 24 wt %, 25 wt % or 30 wt %. The weight ratio of gellan gum to starch may be 0.02 to 0.5, e.g. 0.04, 0.06, 0.09, 0.11, 0.12, 0.16, 0.17, 0.20, 0.23, 0.24 or 0.50.

The starch film-forming composition may also comprise one or more of a plasticizer and a second gelling agent. The plasticizer may include at least one selected from among glycerol, sorbitol, maltitol, erythritol, xylitol, fructose and trehalose. The second gelling agent may include at least one selected from among carrageenan, agar, sodium alginate, low methoxy pectin, high methoxy pectin, amide pectin, high acyl gellan gum, low acyl gellan gum, konjac glucomannan, xanthan gum, locust bean gum, guar gum and pullulan. The content of the plasticizer may be 10 wt % to 35 wt %, e.g. 15 wt %, 17 wt %, 18 wt %, 20 wt %, 25 wt % or 30 wt %.

The starch film-forming composition of the present invention further comprises water, for example 35 wt %-60 wt % of water, e.g. 36 wt %, 39 wt %, 42 wt %, 43 wt %, 46 wt %, 47 wt %, 48 wt %, 49 wt % or 56 wt %. Water can be used to make up the total amount of the composition to 100 wt %.

Soft capsules can be prepared using the starch film-forming compositions of the present invention. The preparation of soft capsules may comprise 1) A) firstly premixing and dispersing the first gelling agent and plasticizer homogeneously, adding into water under stirring, and then heating at a temperature between 60 and 98° C. with stirring until the first gelling agent dissolves; B) adding the starch, and continuing to heat at a temperature between 60 and 98° C. with stirring until the starch dissolves; C) removing air bubbles to obtain a gel mass; 2) encapsulating; and; and 3) drying.

The preparation of soft capsules may comprise 1) A) premixing and dispersing the first gelling agent, the second gelling agent and the plasticizer homogeneously, adding into water under stirring, and then heating at a temperature between 60 and 98° C. with stirring until the first gelling agent and the second gelling agent dissolve; B) adding the starch, and continuing to heat at a temperature between 60 and 98° C. with stirring until the starch dissolves; C) removing air bubbles to obtain a gel mass; 2) encapsulating; and 3) drying. The above starch film-forming composition of the present invention can be prepared into soft capsules with good adhesive and encapsulation properties, and can be used in medicines, food products or cosmetics.

The present invention provides starch film-forming compositions comprising pectin. Preferably, the pectin is at least one selected from among low methoxyl pectin, high methoxyl pectin and amide pectin. The content of pectin may be 0.2 wt %-3.5 wt %, e.g. 0.50 wt %, 1.25 wt %, 1.5 wt %, 2.50 wt % or 3.5 wt %. In this case, the starch film-forming composition may further comprise at least one selected from among carrageenan, agar, sodium alginate, gellan gum, konjac glucomannan, xanthan gum, locust bean gum, guar gum, and pullulan. In one embodiment of this aspect, the starch film-forming composition further comprises gellan gum. For example, the gellan gum is a high acyl gellan gum, a low acyl gellan gum or a gellan gum with a total acyl content of 14-34%, preferably the gellan gum is a gellan gum with a total acyl content of 14-34%, preferably the glyceroyl content in total acyl groups of gellan gum is 12-26% and/or the acetyl content is 2-8%. The content and acyl content of gellan gum may be as defined above.

The starch film-forming composition comprising pectin may also comprise a starch, of which the types and contents are as defined above. In one embodiment, the starch may be hydroxypropyl starch and hydroxypropyl distarch phosphate, for example, each independently of 7 wt-25 wt %, e.g., 8 wt %, 9 wt %, 10 wt %, 11 wt %, 12 wt % %, 13 wt %, 14 wt %, 15 wt %, 16 wt %, 17 wt %, 18 wt %, 19 wt %, 20 wt %, 21 wt %, 22 wt %, 23 wt %, or 24 wt %.

The starch film-forming compositions comprising pectin may also comprise a plasticizer. The types and contents of the plasticizer may be as defined above. The starch film-forming composition comprising pectin may also comprise water. The water content may be as defined above. The present invention demonstrates that starch film-forming compositions without pectin are disintegrated in the stomach and cannot be delivered to the intestine. On the contrary, the starch film-forming composition comprising pectin of the present invention complies with the relevant regulations of enteric capsules in the disintegration test in the Chinese Pharmacopoeia, which is unexpected.

The following examples are presented to further illustrate and explain this invention and should not be taken as limiting in any regard. The scope of this invention is to be determined solely by the scope of the appended claims.

EXAMPLES

Evaluation Method

In order to better illustrate the effects of the present invention, the following standards of a soft capsule are used for evaluation and description.

1) Standards of the strength and toughness of ribbons. A texture analyzer was used and a spherical probe and puncture mode were selected with test speed of 1.0 mm/s. The force values (g) and the corresponding distances (mm) were recorded when the ribbon ruptures. The force applied when the ribbon ruptures represents the strength of the ribbon, and the greater the force, the better the strength of the ribbon. The distance travelled by the probe when the ribbon ruptures represents the toughness of the ribbon. The longer the distance, the better the toughness of the ribbon.

2) Standard of the adhesive property at a seam upon formation. The samples of the examples of the present invention were taken. The capsules were cut at a position other than the seam and were emptied by extrusion of fillers. Then, a ring with two seams at the middle of the capsule was cut off perpendicularly to the seam, which was placed on a glass slide with the two seams perpendicular to the glass slide. The thicknesses of the two seams and the capsule shell were measured under a microscope. The ratio P (%) of the thickness of the seam (which is thinnest) to that of the capsule shell was calculated.

TABLE 1

| | | Score | | | | | |
|---|---|---|---|---|---|---|---|
| Evaluation Standards | Weight | 5 points | 4 points | 3 points | 2 points | 1 point | 0 point |
| strength of the ribbon | 20% | the force ≥ 200 g | 150 g ≤ the force < 200 g | 100 g ≤ the force < 150 | 50 g ≤ the force < 100 | the force < 50 g | failure to form a ribbon |
| toughness of the ribbon | 20% | the distance ≥ 10 mm | 8mm ≤ the distance < 10 mm | 6 mm ≤ the distance < 8 mm | 4 mm ≤ the distance < 6 mm | the distance < 4 mm | failure to form a ribbon |
| seam adhesive property upon formation | 60% | P ≥ 60% | 50% ≤ P < 60% | 40% ≤ P < 50% | 30% ≤ P < 40% | 0 < P < 30% | failure to be shaped |

Standards for evaluating the indicators of the strength, toughness and adhesive property upon formation of the soft capsule ribbon Comprehensive evaluation was carried out using the strength, toughness and seam adhesive property upon formation of the ribbon as indicators, with a full score of 5, and each score (X) indicates:

0 point: Soft capsules cannot be formed;

$0 < X \le 1$: The shaping of the soft capsules is very poor and the soft capsules are easy to leak oil;

$1 < X \le 2$: The shaping of the soft capsules is poor and the soft capsules are easy to leak oil;

$2 < X \le 3$: The shaping of the soft capsules is moderate;

$3 < X \le 4$: The shaping of the soft capsules is excellent;

$4 < X \le 5$: The shaping of the soft capsules is extremely excellent.

Material

The present invention is illustrated by using the following materials without limitation, and the details are as follows.

Gellan gum (total acyl content 14.4%, glyceroyl 12.1%, acetyl 2.3%) (commercially available)

Gellan gum (total acyl content 16.5%, glyceroyl 12.8%, acetyl 3.7%) (commercially available)

Gellan gum (total acyl content 19.0%, glyceroyl 15.1%, acetyl 3.9%) (commercially available)

Gellan gum (total acyl content 27.5%, glyceroyl 19.8%, acetyl 7.7%) (commercially available)

Gellan gum (total acyl content 28.0%, glyceroyl 23.4%, acetyl 4.6%) (commercially available)

Gellan gum (total acyl content 30.6%, glyceroyl 25.1%, acetyl 5.5%) (commercially available)

Gellan gum (total acyl content 33.2%, glyceroyl 25.5%, acetyl content 7.7%) (commercially available)

High acyl gellan gum (total acyl content 37.3%, glyceroyl 20.4%, acetyl 16.9%) (commercially available)

Low acyl gellan gum (total acyl content 11.2%, glyceroyl 8.1%, acetyl 3.1%) (commercially available)

Oxidized starch (commercially available)

Hydroxypropyl starch (commercially available)

Oxidized hydroxypropyl starch (commercially available)

Hydroxypropyl distarch phosphate (commercially available)

Oxidized starch (commercially available)

Acetate starch (commercially available)

Acetylated oxidized starch (commercially available)

Acetylated distarch phosphate (commercially available)

Glycerol (commercially available)

Agar (commercially available)

Locust bean gum (commercially available)

Guar gum (commercially available)

Amide pectin (amidation degree (DA: 5-25%), commercially available)

Low methoxyl pectin (esterification degree (DE: <50%), commercially available)

Konjac glucomannan (commercially available)

Method for Preparing Soft Capsules

The Method Comprises:

1) Gel Mass Preparation: A) firstly premixing and dispersing the first gelling agent and plasticizer homogeneously, adding into water under stirring, and then heating at a temperature between 60 and 98° C. with stirring until the first gelling agent dissolves; if there is a second gelling agent, firstly premixing and dispersing the first gelling agent, the second gelling agent and the plasticizer homogeneously, adding into water under stirring, and then heating at a temperature between 60 and 98° C. with stirring until the first gelling agent and the second gelling agent dissolve; B) adding the starch, and continuing to heat at a temperature between 60 and 98° C. with stirring until the starch dissolves; and C) removing air bubbles to obtain a gel mass;

2) Encapsulation: the soft capsule production line is employed and the gel mass is transported to a spreader box of a soft capsule encapsulation machine, the gel mass is cooled on the surface of a rotating drum to form a ribbon, then soft capsules are formed by extrusion and encapsulation when injecting the filling, and can be further shaped by a rotating cage device.

3) Drying: drying the capsules after forming or shaping with the rotating cage until the moisture content of the shell is 8-25%.

Examples 1-7, Control Examples 1-3

Prepared with the components and contents described in Table 2, soft capsules were tested and scored. The measurement results are shown in Table 2.

TABLE 2

| | Examples 1-7, Control Examples 1-3 | | | | | | | | | |
|---|---|---|---|---|---|---|---|---|---|---|
| Formulation components | Example 1 | Example 2 | Example 3 | Example 4 | Example 5 | Example 6 | Example 7 | Control Example 1 | Control Example 2 | Control Example 3 |
| Gellan gum (total acyl content 14.4%, glyceroyl 12.1%, acetyl 2.3%) | 3% | / | / | / | / | / | / | / | / | / |
| Gellan gum (total acyl content 16.5%, glyceroyl 12.8%, acetyl 3.7%) | / | 3% | / | / | / | / | / | / | / | / |
| Gellan gum (total acyl content 19.0%, glyceroyl 15.1%, acetyl 3.9%) | / | / | 3% | / | / | / | / | / | / | / |
| Gellan gum (total acyl content 27.5%, glyceroyl 19.8%, acetyl 7.7%) | / | / | / | 3% | / | / | / | / | / | / |
| Gellan gum (total acyl content 28.0%, glyceroyl 23.4%, acetyl 4.6%) | / | / | / | / | 3% | / | / | / | / | / |
| Gellan gum (total acyl content 30.6%, glyceroyl 25.1%, acetyl 5.5%) | / | / | / | / | / | 3% | / | / | / | / |
| Gellan gum (total acyl content 33.2%, glyceroyl 25.5%, acetyl content 7.7%) | | | | | | | 3% | | | |
| High acyl gellan gum (total acyl content 37.3%, glyceroyl 20.4%, acetyl 16.9%) | / | / | / | / | / | / | / | 3% | / | 1% |
| Low acyl gellan gum (total acyl content 11.2%, glyceroyl 8.1%, acetyl 3.1%) | / | / | / | / | / | / | / | / | 3% | 2% |
| Oxidized hydroxypropyl starch | 35% | 35% | 35% | 35% | 35% | 35% | 35% | 35% | 35% | 35% |
| Glycerol | 20% | 20% | 20% | 20% | 20% | 20% | 20% | 20% | 20% | 20% |
| Water | 42% | 42% | 42% | 42% | 42% | 42% | 42% | 42% | 42% | 42% |
| Strength of the ribbon | 4 | 4 | 5 | 5 | 5 | 5 | 5 | 3 | 5 | 4 |
| Toughness of the ribbon | 4 | 4 | 4 | 4 | 4 | 4 | 3 | 4 | 2 | 3 |
| Seam adhesive property upon formation | 3 | 4 | 5 | 5 | 5 | 5 | 3 | 1 | 0 | 0 |
| Comprehensive evaluation | 3.4 | 4 | 4.8 | 4.8 | 4.8 | 4.8 | 3 | 2 | 1.4 | 1.4 |

In table 2, the ribbons with good strength, toughness and adhesive property were formed by using the combination of gellan gum with particular acyl content and starch in Examples 1-7, whereas in Control Example 1-2, using the same content of film-forming compositions in this invention, when gellan gum with high acyl content and starch combined, the ribbons were formed with poor strength, few toughness and average adhesive property. In addition, when gellan gum with low acyl content and starch combined, the ribbons were formed with good strength but poor toughness and failed in ribbon formation. In Control Example 3, a compound gel of two gellan gums with different acyl contents was employed, in which the glyceroyl and acetyl contents are close to the particular acyl content range of the present invention, but resulting in a poor adhesive property upon formation. It indicates that the soft capsules prepared by using the combination of gellan gum with particular acyl content of the present invention and starch are superior to the prior art.

Examples 8-18

Prepared with the components and contents described in Table 3, soft capsules were tested and scored. The measurement results are shown in Table 3.

TABLE 3

| | | | | | | Examples 8-18 | | | | | | |
|---|---|---|---|---|---|---|---|---|---|---|---|
| Formulation components | Example 8 | Example 9 | Example 10 | Example 11 | Example 12 | Example 13 | Example 14 | Example 15 | Example 16 | Example 17 | Example 18 |
| Gellan gum (total acyl content 16.5%, glyceroyl 12.8%, acetyl 3.7%) | 1% | 2.0% | 2% | 3% | 3% | 4% | 5% | 6% | 6% | 7% | 8% |
| Oxidized hydroxypropyl starch | 50% | 45.0% | 35% | 35% | 25% | 35% | 30% | 30% | 25% | 30% | 16% |
| Glycerol | 10% | 17.0% | 20% | 15% | 25% | 15% | 20% | 15% | 20% | 15% | 20% |
| Water | 39% | 36.0% | 43% | 47% | 47% | 46% | 45% | 49% | 49% | 48% | 56% |
| Ratio of the gellan gum to the starch | 0.02 | 0.04 | 0.06 | 0.09 | 0.12 | 0.11 | 0.17 | 0.20 | 0.24 | 0.23 | 0.50 |
| Strength of the ribbon | 2 | 3 | 3 | 5 | 5 | 5 | 5 | 5 | 5 | 5 | 5 |
| Toughness of the ribbon | 3 | 3 | 4 | 4 | 4 | 5 | 4 | 4 | 3 | 4 | 4 |
| Seam adhesive property upon formation | 3 | 4 | 4 | 4 | 4 | 4 | 2 | 2 | 2 | 1 | 1 |
| Comprehensive evaluation | 2.8 | 3.6 | 3.8 | 4.2 | 4.2 | 4.4 | 3 | 3 | 2.8 | 2.4 | 2.4 |

In Examples 8-18, with the increase of the amount of gellan gum, the ribbons were formed with higher strength, similar toughness, but lower adhesive property. The starch compositions comprising a particular range of gellan gum to starch ratios are superior to starch compositions not within this range in terms of comprehensive effects, which is unexpected.

Examples 19-25

Prepared with the components and contents described in Table 4, soft capsules were tested and scored. The measurement results are shown in Table 4.

TABLE 4

| | | | | Examples 19-25 | | | |
|---|---|---|---|---|---|---|---|
| Formulation components | Example 19 | Example 20 | Example 21 | Example 22 | Example 23 | Example 24 | Example 25 |
| Gellan gum (total acyl content 19.0%, glyceroyl 15.1%, acetyl 3.9%) | 3% | 3% | 3% | 3% | 3% | 2% | 3% |
| Hydroxypropyl starch | 25% | 35% | / | 24.5% | / | / | / |
| Hydroxypropyl distarch phosphate | / | / | / | 10.5% | / | 25% | 11.9% |
| Oxidized starch | / | / | / | / | 10.5% | / | / |
| Acetate starch | / | / | / | / | / | / | 22.10% |
| Acetylated oxidized starch | / | / | 35% | / | / | / | / |
| Acetylated distarch phosphate | / | / | / | / | 24.50% | / | / |
| Glycerol | 30% | 20% | 20% | 20% | 20% | 25% | 15% |
| Water | 42% | 42% | 42% | 42% | 42% | 48% | 48% |
| Strength of the ribbon | 4 | 5 | 4 | 5 | 4 | 3 | 5 |
| Toughness of the ribbon | 4 | 4 | 4 | 4 | 4 | 4 | 4 |
| Seam adhesive property upon formation | 3 | 3 | 3 | 5 | 3 | 4 | 4 |
| Comprehensive evaluation | 3.4 | 3.6 | 3.4 | 4.8 | 3.4 | 3.8 | 4.2 |

Examples 19-25 illustrate the preparation of the soft capsules using gellan gum with particular acyl content in combination with various types of starch, with a significantly superior effects to the prior art.

Examples 26-31

Prepared with the components and contents described in Table 5, soft capsules were tested and scored. The measurement results are shown below as Table 5.

Examples 32-37

According to the regulation of disintegration test for enteric capsules in Chinese Pharmacopoeia, a disintegration test was carried out with soft capsules prepared from the components and contents described in Table 6. The measurement results are shown below as Table 6.

TABLE 5

| | Examples 26-31 | | | | | |
|---|---|---|---|---|---|---|
| Formulation components | Example 26 | Example 27 | Example 28 | Example 29 | Example 30 | Example 31 |
| Gellan gum (total acyl content 28.0%, glyceroyl 23.4%, acetyl 4.6%) | 2.50% | 2.25% | 2.25% | 2.25% | 2.25% | 2.25% |
| Low acyl gellan gum (total acyl content 11.2%, glyceroyl 8.1%, acetyl 3.1%) | / | / | / | / | / | 0.25% |
| Agar | / | 0.25% | / | / | / | / |
| Locust bean gum | / | / | 0.25% | / | / | / |
| Guar gum | / | / | / | 0.25% | / | / |
| Konjac glucomannan | / | / | / | / | 0.25% | / |
| Hydroxypropyl starch | 17.0% | 17.0% | 17.0% | 17.0% | 17.0% | 17.0% |
| Hydroxypropyl distarch phosphate | 17.0% | 17.0% | 17.0% | 17.0% | 17.0% | 17.0% |
| Glycerol | 18% | 18% | 18% | 18% | 18% | 18% |
| Water | 45.50% | 45.50% | 45.50% | 45.50% | 45.50% | 45.50% |
| Strength of the ribbon | 4 | 4 | 4 | 4 | 4 | 5 |
| Toughness of the ribbon | 3 | 3 | 4 | 4 | 4 | 3 |
| Seam adhesive property upon formation | 4 | 3 | 4 | 4 | 3 | 3 |
| Comprehensive evaluation | 3.8 | 3.2 | 4 | 4 | 3.4 | 3.4 |

In Examples 26-31, the technical effect of preparation of soft capsules by using the gellan gum with particular acyl content and starch in combination with low acyl gellan gum, agar, locust bean gum, guar gum, or konjac glucomannan, respectively, is significantly superior to the prior art.

TABLE 6

| | Example 22, Example 26, Examples 32-37 | | | | | | | |
|---|---|---|---|---|---|---|---|---|
| Formulation components | Example 22 | Example 26 | Example 32 | Example 33 | Example 34 | Example 35 | Example 36 | Example 37 |
| Gellan gum (total acyl content 28.0%, glyceroyl 23.4%, acetyl 4.6%) | / | 2.50% | 2.50% | 3.00% | 3.50% | 2.50% | 3.00% | 3.5% |
| Gellan gum (total acyl content 19.0%, glyceroyl 15.1%, acetyl 3.9%) | 3% | / | / | / | / | / | / | / |
| Low methoxyl pectin (esterification degree DE: <50%) | / | / | / | / | / | 1.25% | 2.5% | 3.5% |
| Amide pectin (amidation degree DA: 5-25%) | / | / | 0.50% | 1.5% | 2.50% | / | / | / |
| Hydroxypropyl starch | 24.5% | 17.0% | 17.0% | 17.0% | 17.0% | 17.0% | 17.0% | 17.0% |
| Hydroxypropyl distarch phosphate | 10.5% | 17.0% | 17.0% | 17.0% | 17.0% | 17.0% | 17.0% | 17.0% |

TABLE 6-continued

| | | Example 22, Example 26, Examples 32-37 | | | | | | | |
|---|---|---|---|---|---|---|---|---|---|
| Formulation components | | Example 22 | Example 26 | Example 32 | Example 33 | Example 34 | Example 35 | Example 36 | Example 37 |
| Glycerol | | 20% | 18% | 18% | 18% | 18% | 18% | 18% | 18% |
| Water | | 42% | 45.5% | 45.00% | 43.50% | 42.00% | 44.25% | 42.5% | 41% |
| Disinte-gration time (minutes) | First check in hydrochloric acid solution (9 → 1000) for 2 h, the capsule shell should not have cracks or disintegration | Disinte-gration in 30 minutes | Disinte-gration in 30 minutes | No cracks or disinte-gration | No cracks or disinte-gration | No cracks or disinte-gration | No cracks or disinte-gration | No cracks or disinte-gration | No cracks or disinte-gration |
| | Completely disintegrated within 1 h in phosphate buffer (PH 6.8) | / | / | 23 minutes | 24 minutes | 20 minutes | 22 minutes | 18 minutes | 17 minutes |

According to the relevant regulations of enteric capsules in the disintegration test of "Chinese Pharmacopoeia", the disintegration time of the samples in Example 22, Example 26, and Examples 32-37 were tested, with the results indicating that the samples in Example 22 and Example 26 which were checked in hydrochloric acid solution (9→4000) without the discs, disintegrated completely within 60 minutes; while the samples in Examples 32-37 which were checked in the hydrochloric acid solution (9→1000) without the discs, did not disintegrate in 120 minutes, and then completely disintegrated within 60 minutes when detected in phosphate buffer (PH 6.8) with one disc added to each tube, which meets the requirements for the disintegration time limit of enteric capsules in the disintegration test of "Chinese Pharmacopoeia". Therefore, the soft capsules prepared using the gellan gum with particular acyl content and starch in combination with pectin (such as low methoxyl pectin or amide pectin) in the present invention may meet the disintegration time limit of enteric soft capsules.

In the present invention, from the composition of gellan gum with particular acyl content and starch, soft capsules were prepared with increasing film-forming strength and toughness but reducing adhesive property as the proportion of gellan gum increases within a particular range. The soft capsules prepared by using the composition of the present invention having the gellan gum with particular acyl content and starch are significantly superior to those in the prior art in terms of the ribbon strength, toughness and adhesive property upon formation. The composition of the present application can fully meet the requirements for industrial production of soft capsules and can be used as an alternative in soft capsule technology.

The above examples are preferred embodiments of the present invention, but the present invention are not limited to the above examples, and any other changes, modifications, substitutions, combinations, simplification made without departing from the spirit and principle of the present invention should be deemed as equivalent replacements, and are all included in the claimed scope of the present invention.

The invention claimed is:

1. A starch film-forming composition comprising:
A. a first gelling agent; and
B. a starch;
wherein the first gelling agent is a gellan gum which has a total acyl content ranging from 14% to 34%, wherein the content of glyceroyl of the gellan gum ranges from 12% to 26%, and the content of acetyl of the gellan gum ranges from 2% to 8%, the gellan gum in the starch film-forming composition has a single gelling temperature, and the weight ratio between the gellan gum having a single gelling temperature and the starch ranges from 0.02 to 0.5.

2. The starch film-forming composition of claim 1, wherein the content of starch in the starch film-forming composition ranges from 15 wt % to 50 wt %.

3. The starch film-forming composition of claim 1, wherein the content of gellan gum in the starch film-forming composition ranges from 1 wt % to 8 wt %.

4. The starch film-forming composition of claim 1, wherein the starch is a natural starch, including at least one selected from among wheat starch, waxy corn starch, pea starch, corn starch, potato starch and tapioca starch.

5. The starch film-forming composition of claim 1, wherein the starch is a starch derivative, and the starch derivative is at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin.

6. The starch film-forming composition of claim 1, wherein the starch film-forming composition further comprises plasticizer, the content of the plasticizer in the starch film-forming composition ranging from 10 wt % to 35 wt %.

7. The starch film-forming composition of claim 1, wherein the starch film-forming composition further comprises a second gelling agent, the second gelling agent is at least one selected from among carrageenan, agar, sodium alginate, pectin, konjac glucomannan, xanthan gum, locust bean gum, guar gum and pullulan.

8. The starch film-forming composition of claim 1, further comprising water, wherein the content of water in the starch film-forming composition ranges from 35 wt % to 60 wt %.

9. A method for preparing a capsule shell using the starch film-forming composition of claim 6, comprising 1) A) firstly premixing and dispersing the first gelling agent and plasticizer homogeneously to form a mixture, and adding the mixture into water under stirring, and then heating it at a temperature between 60 and 98° C. with stirring until the first gelling agent dissolves; B) adding the starch, and continuing to heat at a temperature between 60 and 98° C. with stirring until the starch dissolves; C) removing air bubbles to obtain a gel mass;

2) forming the capsule shell from the gel mass; and 3) drying the capsule shell.

10. The method for preparing a capsule shell of claim 9, wherein the step A) further comprises adding a second gelling agent; and the step A) is a step for premixing and dispersing the first gelling agent, the second gelling agent and the plasticizer homogeneously to form a mixture, adding the mixture into water under stirring, and then heating it at a temperature between 60 and 98° C. with stirring until the first gelling agent and the second gelling agent dissolve.

11. A capsule shell comprising the starch film-forming composition of claim 1.

12. The capsule shell of claim 11, wherein the capsule shell further comprises water, and wherein the content of water in the capsule shell ranges from 8wt % to 25 wt %.

13. The starch film-forming composition of claim 1, wherein the starch is a natural starch, including at least one selected from among wheat starch, waxy corn starch, pea starch, corn starch, potato starch and tapioca starch, or wherein the starch is a starch derivative, and the starch derivative is at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin.

14. The starch film-forming composition of claim 2, wherein the starch is a natural starch, including at least one selected from among wheat starch, waxy corn starch, pea starch, corn starch, potato starch and tapioca starch, or wherein the starch is a starch derivative, and the starch derivative is at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin.

15. The starch film-forming composition of claim 3, wherein the starch is a natural starch, including at least one selected from among wheat starch, waxy corn starch, pea starch, corn starch, potato starch and tapioca starch, or wherein the starch is a starch derivative, and the starch derivative is at least one selected from among acid-treated starch, hydroxypropyl starch, oxidized starch, acetate starch, oxidized hydroxypropyl starch, hydroxypropyl distarch phosphate, starch phosphate, sodium starch octenyl succinate, acetylated distarch phosphate and dextrin.

16. The starch film-forming composition of claim 1, wherein the content of gellan gum in the starch film-forming composition ranges from 2 wt % to 7 wt %.

17. The starch film-forming composition of claim 6, wherein the plasticizer is at least one selected from glycerol, sorbitol, maltitol, erythritol, xylitol, fructose and trehalose.

18. The starch film-forming composition of claim 7, wherein the content of the second gelling agent in the starch film-forming composition ranges from 0.2 wt % to 2.5 wt %.

19. The starch film-forming composition of claim 7, wherein the pectin is at least one selected from low methoxyl pectin, high methoxyl pectin and amide pectin.

* * * * *